United States Patent
Smith

(12) 
(10) Patent No.: US 6,331,708 B2
(45) Date of Patent: Dec. 18, 2001

(54) EXAMINING A DIAMOND

(75) Inventor: Martin Phillip Smith, Wargrave (GB)

(73) Assignee: Gersan Establishment (LI)

( * ) Notice: Subject to any disclaimer, the term of this patent is extended or adjusted under 35 U.S.C. 154(b) by 0 days.

(21) Appl. No.: 09/766,338

(22) Filed: Jan. 19, 2001

Related U.S. Application Data

(63) Continuation of application No. 09/011,342, filed as application No. PCT/GB96/01752 on Jul. 22, 1996, now abandoned.

(30) Foreign Application Priority Data

Jul. 24, 1995 (GB) .................................................. 9515144

(51) Int. Cl.$^7$ .................................................. G01N 21/56
(52) U.S. Cl. .................... 250/483.1; 250/372; 250/559.4
(58) Field of Search .............................. 250/483.1, 559.4, 250/372, 461.1

(56) References Cited

U.S. PATENT DOCUMENTS

| | | | |
|---|---|---|---|
| 3,594,583 | | 7/1971 | Sheldon ................................ 250/220 |
| 3,947,120 | | 3/1976 | Bar-Isaac et al. ...................... 356/30 |
| 5,536,943 | * | 7/1996 | Smith et al. .......................... 250/372 |
| 5,670,777 | | 9/1997 | Inushima et al. .................. 250/214.1 |
| 5,811,824 | * | 9/1998 | Smith et al. ....................... 250/559.4 |
| 6,239,867 | * | 5/2001 | Aggarwal ............................... 356/30 |

* cited by examiner

*Primary Examiner*—Constantine Hannaher
*Assistant Examiner*—Otilia Gabor
(74) *Attorney, Agent, or Firm*—Cesari and McKenna

(57) ABSTRACT

In order to test whether a diamond has had a layer a synthetic diamond deposited thereon, the diamond is radiated with ultraviolet radiation so as to form a pattern of beams of refracted and reflected radiation, the pattern of refracted and reflected radiation being observed on a screen behind the diamond.

25 Claims, 2 Drawing Sheets

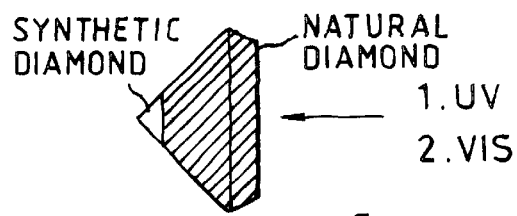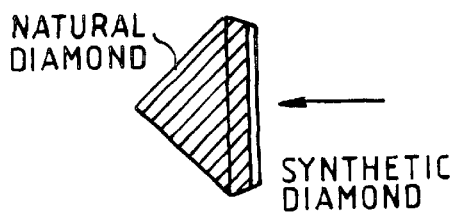
Fig. 2a  Fig. 2b
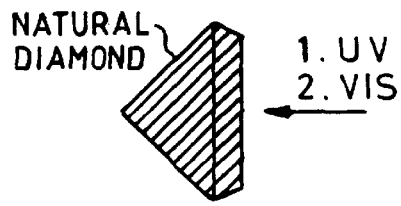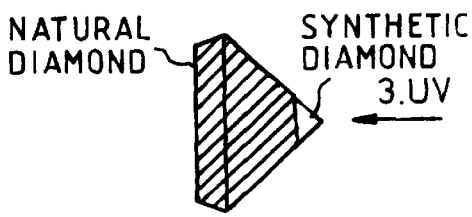
Fig. 2c  Fig. 2d
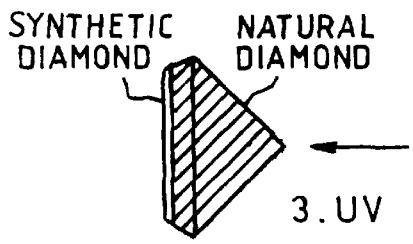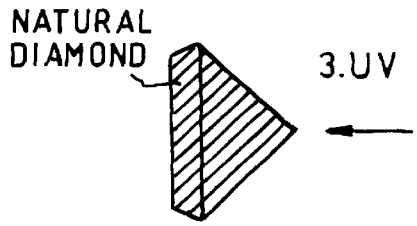
Fig. 2e  Fig. 2f

EXAMINING A DIAMOND

RELATED APPLICATION

This application is a continuation of Ser. No. 09/011,342, filed Mar. 27, 1998, now abandoned, of which is a 371 of PCT/GB96/01752, filed Jul. 22, 1996.

BACKGROUND TO THE INVENTION

The present invention relates to a method of and apparatus for testing whether a natural diamond has had a layer of synthetic diamond deposited thereon. This is of particular importance in testing whether the diamond is wholly natural or whether any part of it comprises CVD diamond material and also in locating such material if present.

Synthetic diamond material may be deposited on an uncut or part processed natural diamond which is then worked, for example, into a round brilliant cut. Alternatively, the synthetic diamond material coating may be deposited onto a fully fashioned brilliant stone after working of the stone. The thickness of the synthetic diamond material layer may be very thin (it could be in the range from 5 microns to 10 microns) but the present invention may also be used to detect thicker layers.

The value of a diamond is in part dependent upon its weight. Accordingly, synthetic diamond material may be deposited onto natural gem diamonds, before or after cutting of the diamond, to increase the weight of the finished product.

However, the value of a diamond also resides in its qualities of authenticity and uniqueness and in the fact that it is an entirely natural (ie mined) product. Thus, a diamond that has not been enlarged by deposition of synthetic diamond material has a value over a diamond which has.

Over the years, a number of methods of synthesising diamond material have been developed. One of these methods is the chemical vapour deposition (CVD) technique, which is a low pressure technique involving deposition of synthetic diamond (referred to as CVD diamond material in this specification) onto a substrate from a gas. CVD is the most likely way in which synthetic diamond will be deposited on a diamond, although alternative techniques such as physical vapour deposition have been proposed. A diamond artificially enlarged by deposition of CVD or similar diamond material is referred to in this specification as a "CVD/natural diamond doublet".

CVD diamond material may be deposited on a non-diamond or diamond substrate. In the latter case, the CVD diamond material can replicate the structure of the diamond substrate (referred to as "homoepitaxial growth"). The CVD/natural diamond doublet produced can be identical in appearance, density and other common physical properties to an entirely natural stone and there may be a problem in identifying such a CVD/natural diamond doublet.

A method of testing whether a diamond has had a layer of synthetic diamond deposited thereon is disclosed in British Patent Application No. 9401354.7 published as GB2286251A. A plurality of parts of the diamond are irradiated with radiation substantially of wavelength substantially in the range 230 nm to 320 nm and the transmission of the irradiating radiation by the diamond is observed.

The invention of GB 9401354.7 is based upon the observation that where different zones of a diamond show differences in their absorption of radiation substantially of wavelength substantially 230 nm to 320 nm, it may be concluded that the diamond in question has a layer of synthetic diamond deposited thereon. It is further observed that if all zones of a diamond strongly absorb radiation substantially of wavelength substantially 230 nm to 320 nm, the diamond may be classified as almost certainly a wholly natural diamond.

The intensity of radiation transmitted by the zones of the diamond may be investigated using an imaging apparatus or by placing the diamond in an integrating sphere. Preferably, an image of the diamond is formed against a dark or light background.

It is an object of the present invention to provide a method of and apparatus for testing whether a diamond has had a layer of synthetic diamond deposited thereon, in which relatively simple imaging apparatus is used and an expensive integrating sphere is not required.

It is desired that the apparatus should be simple and inexpensive and may be put into operation by a person with relatively little training. The method and apparatus should be capable of being operated reliably and consistently by a practised jeweller who has no training in laboratory gemological analysis.

THE INVENTION

The present invention provides a method of testing whether a diamond has had a layer of synthetic diamond deposited thereon, comprising:

directing a beam of ultraviolet radiation towards a face of a diamond, so as to form a pattern of beams of radiation due to refraction and reflection of the irradiating radiation, and observing the pattern of such beams of radiation substantially of wavelength substantially in the range 230 nm to 320 nm The present invention uses the same principles of absorption of certain wavelengths of ultra-violet radiation by certain types of diamond as used in GB 9401354.7.

It is known from documents such as U.S. Pat. No. 3,947,120 that where light is directed towards a cut gemstone, a pattern of spots of reflected and refracted radiation may be produced which is characteristic of each gemstone The present inventors have discovered that the different interaction of different types of diamond with ultraviolet radiation of the waveband in question can affect the pattern of spots obtained and help to identify superficial synthetic diamond layers.

In simple terms, substantial differences in the complexity and intensity of beams produced by different parts of the diamond (allowing for the shape of the diamond) indicate the presence of synthetic layers on the diamond.

In detail, the invention is based upon the observation that the majority of natural diamonds are classified as type IaA or IaAB and very strongly absorb ultraviolet radiation of wavelength shorter than approximately 320 nm, whereas a synthetic diamond layer will normally be of a type which strongly absorbs ultraviolet radiation of wavelength shorter than approximately 230 nm, in particular type II diamond. Thus natural diamond is generally expected to give weak or unobservable reflected and refracted beams with radiation of wavelength shorter than 320 nm.

A synthetic diamond layer is generally expected to give a complex pattern of reflected and refracted beams. Any diamonds which give results suggesting the presence of a synthetic layer should be referred for further testing.

Preferably, substantially the whole of the present face of the diamond is irradiated. This allows a complete pattern of beams to be formed and observed.

In principle, a single observation of the pattern of refracted and reflected beams of radiation could be sufficient to reveal the presence of a layer of synthetic diamond material. If, for example, a substantially symmetrical face of the diamond is exposed to the radiation and an asymmetric pattern of beams is obtained, the presence of layers of synthetic diamond may be suspected.

However, it is preferable to direct the beam of radiation to the diamond from a number of directions in succession and to compare the patterns obtained. Interpretation of the results will be discussed further below.

It may be sufficient to test only a few faces (maybe only two) in order to detect a difference in the pattern of reflected and refracted beams. Preferably, however, a large number of faces are irradiated in succession.

The diamond may be irradiated with suitable radiation (as discussed below) by exposing it to radiation from a suitable source. The irradiating radiation may be focussed if necessary.

The beam of irradiating radiation may be of size less than the presented face of the diamond but is preferably greater in size.

In the invention, the pattern of reflected and refracted beams observed does not correspond to the image of the diamond. What is observed is the pattern produced where the reflected and refracted beams intercept a notional plane displaced from the diamond. A screen or scanning means may be placed at this notional plane. The scanning means may measure the intensity of light at each point on the notional plane to thereby record the pattern of reflected and refracted beams.

Preferably, the pattern of reflected and refracted beams is observed by placing a screen a predetermined distance from the diamond so that the beams of reflected and refracted radiation impinge upon the screen, and detecting the pattern on the screen. Preferably an image of the pattern on the screen is formed.

The screen may be movable and angularly adjustable with respect to the diamond.

The screen is particularly preferably placed on the direction-of-irradiation side of the diamond, so that back-scattered reflected and refracted beams are observed. In this case, it is preferable that the irradiating radiation passes to the diamond through an aperture in the screen.

The screen may comprise an ultraviolet sensitive fluorescent screen for revealing the pattern of beams produced. In this case, the screen may be observed by eye through an observing means having a filter for cutting out hazardous irradiating radiation.

Alternatively, a camera may be used to observe the screen.

The radiation observed could comprise a narrow band of wavelengths lying substantially in the above mentioned range, a number of such narrow bands or it could be a relatively broad band. Optionally, it falls substantially in the range 230 nm to 300 nm, being preferably below 290 nm. The radiation observed may comprise some radiation of wavelength falling outside the range 230 nm to 320 nm but such radiation is preferably of sufficiently low intensity to avoid confusing the beams observed at the wavelength of interest.

The radiation may be generated by a suitable laser, e.g. a 248 nm krypton fluoride excimer laser.

In order to observe radiation substantially of wavelength substantially 230 nm to 320 nm, the diamond may be irradiated only with such radiation (produced by a laser or by a wider band source having a filter). Alternatively, the diamond may be irradiated with radiation of a broader range of wavelengths, wavelength selective means such as a filter being provided between the diamond and the screen or imaging means to pass radiation of wavelength substantially 230 nm to 320 nm. If the diamond is irradiated with radiation substantially of wavelength substantially 230 nm to 320 nm, wavelength selective means may also be provided to exclude radiation produced by fluorescence excited by the incident ultraviolet radiation. Normally, however, the intensity of fluorescence is not strong enough to require filtering.

When the irradiating radiation is incident on a zone of the diamond, it will generally be strongly absorbed or partially transmitted. The radiation transmitted by a zone of the diamond will be refracted inside the diamond and some transmitted radiation may be observed leaving the surface of the diamond. Thus, a pattern of beams of reflected and refracted radiation will be produced when a face of a diamond is irradiated.

The intensity of reflected beams from any given surface will depend in part upon the transmissivity of that surface and in part upon the angle of incidence of the radiation upon the surface. The intensity of refracted radiation beams will depend in part upon the transmissivity of the diamond material of a part observed and in part on its thickness.

Natural diamond usually has such a high absorption coefficient at the wavelengths in question that incident radiation is almost totally absorbed.

CVD or other synthetic diamond material surface layers are commonly of a type that at least partially transmits the radiation, in particular type II diamond.

Thus, where a face of a diamond is irradiated normally and substantially no refracted beams are produced other than the reflection normal to the face, it may be concluded that the face is probably natural diamond.

Where a face is normally irradiated and pattern of weak reflected and refracted beams is observed, the presence of a thin layer of synthetic diamond is indicated.

Where a face of a diamond is irradiated at a relatively large angle off the normal (referred to as "oblique irradiation"), and a relatively weak and simple pattern of reflected beams is produced, it may be concluded that the face irradiated comprises natural diamond. If, however, a pattern of relatively strong and complex reflected and refracted beams is observed, the presence of synthetic diamond material is suggested.

Any suggestion of synthetic diamond material should be followed up with further testing, as the reflected and refracted beams may be due to natural diamond of a rare type.

If a diamond is irradiated on a face which is substantially symmetrical, and a pattern which is grossly unsymmetrical (for example, light on one side, dark on the other) is produced, it may be concluded that the sides of the face of the diamond presented are of different composition.

Because of the complex pattern of light paths within a brilliant-cut diamond, the two parts of a CVD/natural diamond doublet may not be immediately apparent. It may be necessary to manipulate a CVD/natural diamond doublet while it is being viewed, in order to clearly see the two parts of the diamond.

In order to assist in the interpretation of the patterns of reflected and refracted beams produced when a diamond is irradiated with the first mentioned radiation, the diamond may be irradiated with radiation which is substantially transmitted by all types of diamond, such as visible radiation, so that a reference pattern may be formed. This pattern may then be compared to a pattern obtained using the first mentioned radiation, preferably with the diamond in the same configuration.

The reference pattern is expected to show relatively strong and complex patterns of reflected and refracted radiation for all types of diamond.

The present invention further provides apparatus for testing whether a diamond has had a layer of synthetic diamond deposited thereon, comprising means for irradiating the diamond with ultraviolet radiation, and a screen mounted a predetermined distance from the diamond so that the screen intercepts a pattern of beams of reflected and refracted radiation produced when a diamond is irradiated, and means for allowing the pattern of beams of radiation substantially of wavelength substantially in the range of 230 nm to 320 nm on the screen to be observed The apparatus according to the invention could be automated to automatically interpret and analyse images or readings produced. However, this is not preferred as a simple system in which the images are interpreted by the operator is practicable and cheaper.

The invention will be further described by way of example only, with reference to the accompanying drawings, in which:

BRIEF DESCRIPTION OF THE DRAWINGS

FIGS. 2a–2f are schematic illustrations of patterns of reflected and refracted beams produced according to the present invention when various diamonds are irradiated with ultraviolet or visible radiation.

DETAILED DESCRIPTION OF THE DRAWINGS

Figure 1:
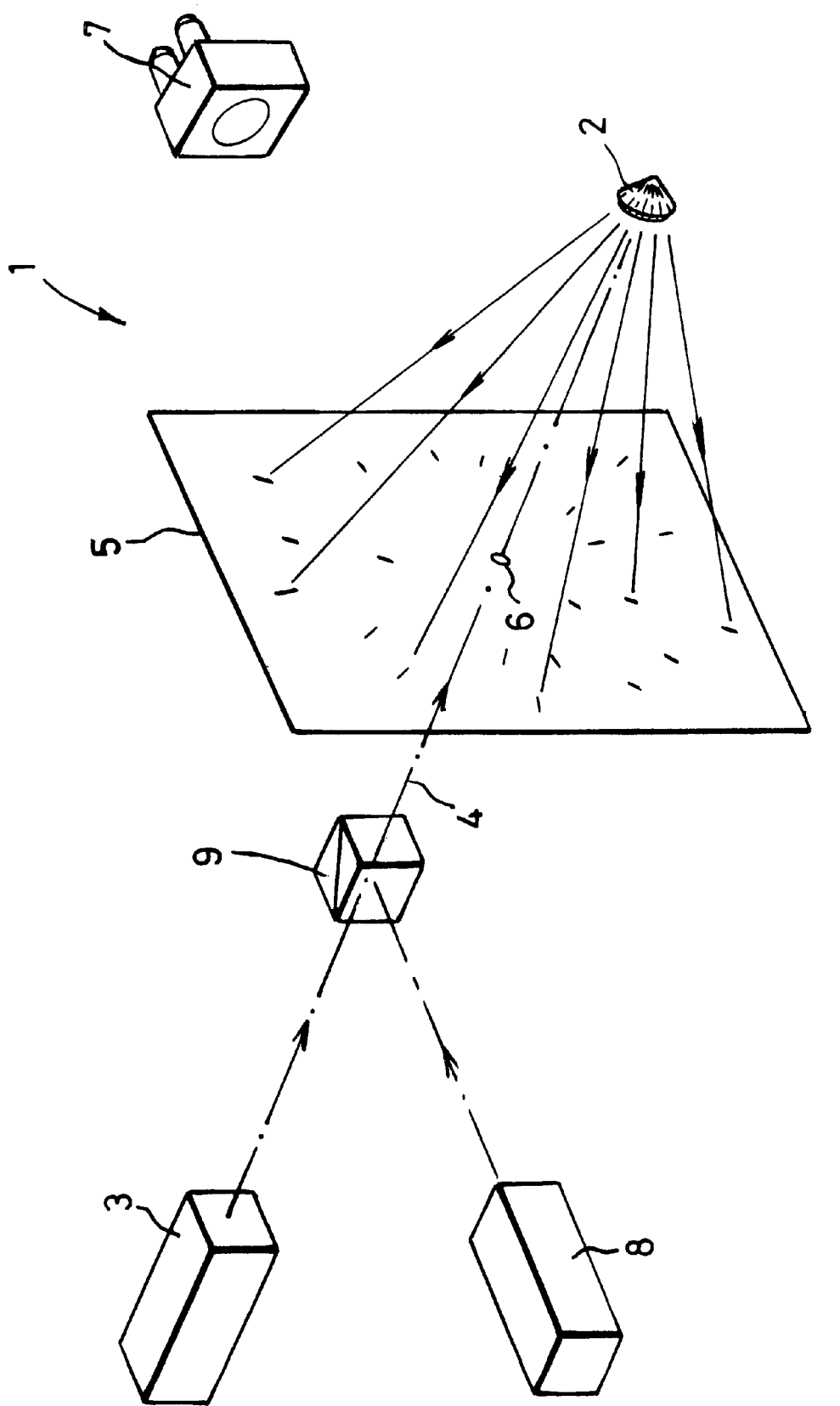
FIG. 1 is a schematic illustration of apparatus according to the invention.

In the apparatus shown schematically as 1 in FIG. 1, a diamond 2 is irradiated with radiation of wavelength substantially in the range 230–320 nm by a laser 3. The laser beam 4 is directed through a screen 5, through an aperture 6 provided in the middle thereof. When the beam of radiation 4 is incident upon the diamond 2, a pattern of beams of reflected and refracted radiation may be produced. The pattern produced in the back-scattered direction is studied in the embodiment shown in FIG. 1. The screen 5 is movable and angularly adjustable. The pattern is studied by arranging the screen 5 at a distance from the diamond 2 such that substantially all the beams of reflected and refracted radiation are intercepted by the screen. Typically, for a screen of size 100 mm×100 mm, the distance between the diamond and the screen is circa 60 mm.

An observing means 7 is provided for observing the pattern of reflected and refracted beams formed on the screen 5.

The screen 5 is a UV fluorescent screen, which generates spots of visible light where ultraviolet radiation of wavelength 230–320 nm is incident upon it. The observing means 7 may comprise a suitable optical device with a filter for filtering out radiation of ultraviolet wavelengths, which can be dangerous to the eye.

The whole apparatus 1, except for the observing means 7 may be enclosed in a light-tight box, for excluding external radiation which may confuse the pattern on the screen and for containing the dangerous UV radiation. The observing means 7 may be mounted at a suitable position within the walls for the light-tight box so that an observer can see the pattern on the screen 5.

In order to provide a reference pattern, a laser 8 producing light of a visible wavelength is provided. A beam splitter 9 is provided in the path of beam 4 so that the visible radiation from laser 8 may be directed down the path of the irradiating radiation 4 from laser 3. Preferably, lasers 3 and 8 are used in alternation so that the different patterns produced by the different types of radiation may be compared.

In FIGS. 2a to 2f, the results of irradiation of a diamond according to the invention are shown.

Three cases were studied:

a. A diamond which is a CVD/natural diamond doublet, with the synthetic part on the culet of the diamond, b. A CVD/natural diamond doublet in which the synthetic diamond is formed on the table of the diamond, c. A completely natural diamond In each case, the diamond is a cut diamond having a brilliant cut, being the type of cut which will be most frequently encountered. The technique is, however, applicable to all diamond cuts, including fancy cuts, although a more complex and careful interpretation of the returned pattern may be required for fancy cuts.

The diamond is irradiated using the three steps:

1. irradiation of the table in a normal direction using ultraviolet radiation of wavelength substantially in the range 230–320 nm, 2. normal irradiation of the table using visible radiation, and 3. irradiation of the culet using ultraviolet radiation substantially of wavelength falling in the range substantially 230–320 nm.

The above-mentioned three types of diamond can be distinguished by the different patterns of reflected and refracted radiation that they produce.

In FIGS. 2a–2f, sport of high intensity are shown as a solid black dot, spots of medium intensity are shown as short complete lines and spots of low intensity are shown as short, dotted lines.

In FIGS. 2a–2c, the results of steps 1 and 2 are shown on a single screen for comparison, though in practice they would be separate.

FIG. 2a shows the results of steps 1 and 2 with a diamond (a).

The pattern on the screen in step 1 is observed to comprise a single high intensity spot 10 produced by normal reflection of the irradiating radiation.

In step 2, a complex relatively intense pattern of spots 11 is observed.

FIG. 2b shows the results of steps 1 and 2 with diamond (b) In step 1, a pattern of reflected and refracted beams 12 of relatively low intensity is observed. In step 2, a pattern of reflected and refracted beams of relatively high intensity is produced. The patterns are different, as the refractive index of diamond at the ultraviolet wavelengths observed is different to the refractive index of visible radiation.

FIG. 2c shows the results of steps 1 and 2 with diamond (c). In step 1 a single relatively high intensity spot 14 is produced by normally reflected radiation only. In step 2, a relatively intense and complex pattern of reflected and refracted beams 15 is produced. The patterns observed in FIG. 2c are similar to those shown in FIG. 2a.

FIG. 2d shows the results of step 3 with the diamond (a). A relatively complex pattern of strong reflected and refracted beams 17 is produced, together with a strong beam 16 due to radiation reflected normally from the culet (assuming that there is a culet facet).

FIG. 2e shows the results of step 3 with diamond (b). A relatively weak simple pattern of reflected beams 18 is produced due to reflection off the cut surfaces around the culet.

FIG. 2f shows the results of step 3 with diamond (c). A simple pattern of relatively weak reflected beams 19 is produced.

In the apparatus shown in FIG. 1, the ultraviolet laser may comprise a 248 nm krypton fluoride excimer laser from Potomac lasers. The laser 8 may comprise a 635 nm laser diode or 633 nm HeNe laser from Vector Technology/Melles Griot. The beam splitter 9 is manufactured by Spindler and Hoyer and the ultraviolet sensitive fluorescent screen is supplied by Levy-Hill Ltd. If a camera is used to observe the screen 5, it may be a CCD camera coupled to a computer for analysing the spot pattern produced.

What is claimed is:

1. A method of testing whether a diamond has had a layer of synthetic diamond deposited thereon, comprising:
    directing a beam of ultraviolet radiation towards a face of the diamond, so as to form a pattern of beams of radiation due to refraction and reflection of the irradiating radiation, and
    observing the pattern of beams of radiation substantially of wavelength substantially in the range of 230 nm to 320 nm whereby if the reflected and refracted beams are weak or unobservable, it is indicated that said face is formed of natural diamond, and if said pattern is complex, it is indicated that said face is at least partly formed of synthetic diamond.

2. A method of testing whether a diamond has had a layer of synthetic diamond deposited thereon, comprising:
    directing a beam of ultraviolet radiation towards a face of a diamond so as to form a pattern of beams of radiation due to refraction and reflection of the irradiating radiation and observing the pattern of beams of radiation substantially of wavelength substantially in the range of 230 nm to 320 nm;
    directing a beam of ultraviolet radiation to a second face of the diamond and observing the pattern of beams of radiation substantially of wavelengths substantially in the range of 230 nm to 320 nm produced by the second surface, and comparing the pattern of beams of the first-mentioned face of the diamond and the second face of the diamond.

3. A method according to claims 1 or 2, wherein a large number of faces of the diamond are irradiated in succession.

4. A method according to claim 1 or 2, wherein the pattern of reflected and refracted beams is observed by placing a screen a predetermined distance from the diamond so that the beams of refracted and reflected radiation impinge upon the screen and detecting the pattern of beams on the screen.

5. A method according to claim 4, wherein an image of the screen is formed.

6. A method according to claim 4, wherein the screen is placed on the direction-of-irradiation side of the diamond, so that back-scattered reflected and refracted beams are observed.

7. A method according to claim 4, wherein the screen comprises an ultraviolet sensitive fluorescent screen.

8. A method of testing whether a diamond has had a layer of synthetic diamond deposited thereon, comprising:
    directing a beam of ultraviolet radiation towards a face of the diamond so as to form a pattern of beams of radiation due to refraction and reflection of the irradiating radiation;
    forming a reference image by irradiating the face of the diamond with radiation which is substantially transmitted by all types of diamond, and
    observing the pattern of beams of radiation substantially of wavelength substantially in the range of 230 nm to 320 nm whereby if the reflected and refracted beams are weak or unobservable, it is indicated that said face is formed of natural diamond, and if said pattern is complex, it is indicated that said face is at least partly formed of synthetic diamond.

9. Apparatus for testing whether a diamond has had a layer of synthetic diamond deposited thereon, comprising:
    means for irradiating the diamond with ultraviolet radiation;
    a screen mounted at a predetermined distance from the diamond so that the screen intercepts a pattern of beams of reflected and refracted radiation produced when a diamond is irradiated, and
    means for allowing the pattern of beams of radiation substantially of wavelength substantially in the range 230 nm to 320 nm on the screen to be observed.

10. Apparatus according to claim 9, wherein the screen comprises an ultraviolet fluorescent screen.

11. Apparatus according to claim 9 or 10, wherein the irradiating means comprises a laser.

12. Apparatus according to claims 9 or 10, further comprising means for irradiating the diamond with radiation which is substantially transmitted by all types of diamond.

13. Apparatus according to claims 9 or 10, wherein the screen is placed on the direction-of-irradiation side of the diamond for intercepting back-scattered reflected and refracted beams from the diamond.

14. A method of testing whether a diamond has had a layer of synthetic diamond deposited thereon, comprising:
    directing a beam of ultraviolet radiation towards a face of the diamond, so as to form a pattern of spots due to beams of radiation caused by refraction and reflection of the irradiating radiation, and
    observing the pattern of spots due to beams of radiation substantially of wavelength substantially in the range of 230 nm to 320 nm whereby if the reflected and refracted spots are weak or unobservable, it is indicated that said face is formed of natural diamond, and if said pattern is complex, it is indicated that said face is at least partly formed of synthetic diamond.

15. A method according to claim 14, wherein the beams of radiation due to refraction and reflection form a pattern of spots at a notional surface which is spaced from the diamond, which pattern is observed.

16. A method according to claim 14, wherein the radiation irradiates substantially all of the respective face of the diamond.

17. Apparatus for testing whether a diamond has had a layer of synthetic diamond deposited thereon, comprising:
    a laser for irradiating the diamond with ultraviolet radiation in the range 230 nm to 320 nm, and
    a screen mounted at a predetermined distance from the diamond so that the screen intercepts a pattern of beams of reflected and refracted radiation produced when the diamond is irradiated and the beams form spots on the screen,
    whereby the screen allows the pattern of spots to be observed.

18. Apparatus for testing whether a diamond has had a layer of synthetic diamond deposited thereon, comprising:
    a laser for irradiating the diamond with ultraviolet radiation in the range 230 nm to 320 nm; and
    a laser for irradiating the diamond with radiation which is substantially transmitted by all types of diamonds;
    a screen mounted at a predetermined distance from the diamond so that the screen intercepts a pattern of beams of reflected and refracted radiation produced when a diamond is irradiated and the beams form spots on the screen, whereby, when the diamond is irradiated with the ultraviolet radiation, the screen allows the pattern of spots to be observed, and whereby, when the diamond is irradiated with radiation which is substantially transmitted by all types of diamond, the resulting pattern of spots can be compared with that produced when the diamond is irradiated with ultraviolet radiation.

19. A method of testing whether a natural diamond has had a layer of synthetic diamond deposited thereon, comprising:

directing a beam of ultraviolet radiation towards a face of the diamond, so as to form a pattern of beams of radiation due to refraction and reflection of the irradiating radiation;

placing an ultraviolet-sensitive fluorescent screen at a distance from the diamond so that the beams of refracted and reflected radiation impinge upon the screen and form a pattern of spots thereon;

providing a filter for cutting out hazardous radiation, whereby the screen can be observed by eye;

observing by eye on the screen the pattern of spots due to beams of radiation substantially of wavelength substantially in the range 230 nm to 320 nm, to thereby determine whether the diamond has had a layer of synthetic diamond deposited thereon.

20. A method of testing whether a natural diamond has had a layer of synthetic diamond deposited thereon, comprising:

directing a beam of ultraviolet radiation towards a face of the diamond, so as to form a pattern of beams of radiation due to refraction and reflection of the irradiating radiation;

placing an ultraviolet-sensitive fluorescent screen which fluoresces when ultraviolet radiation of wavelength substantially in the range 230 nm to 320 nm is incident upon it at a distance from the diamond so that the beams of refracted and reflected radiation impinge upon the screen;

providing a filter for cutting out hazardous radiation, whereby the screen can be observed by eye;

observing by eye on the screen the pattern of spots due to beams of radiation substantially of wavelength substantially in the range 230 nm to 320 nm, to thereby determine whether the diamond has had a layer of synthetic diamond deposited thereon.

21. A method of testing whether a natural diamond has had a layer of synthetic diamond deposited thereon, comprising:

directing a beam of ultraviolet radiation towards a face of the diamond at an angle substantially normal to said face, so as to form a pattern of beams of radiation due to refraction and reflection of the irradiating radiation; and observing the pattern of beams of radiation substantially of wavelength substantially in the range 230 nm to 320 nm, whereby if substantially no refracted beams are produced other than a reflection normal to said face, it is indicated that said face is probably formed of natural diamond, and if a pattern of weak reflected and refracted beams is observed, the presence of a layer of synthetic diamond on said face is indicated.

22. A method of testing whether a natural diamond has had a layer of synthetic diamond deposited thereon, comprising:

directing a beam of ultraviolet radiation towards a face of the diamond at a large angle from the normal to the face, so as to form a pattern of beams of radiation due to refraction and reflection of the irradiating radiation; and observing the pattern of beams of radiation substantially of wavelength substantially in the range 230 nm to 320 nm, whereby if a relatively weak and simple pattern of reflected beams is observed, it is indicated that said face is formed of natural diamond, and if a pattern of relatively strong and complex reflected and refracted beams is observed, the presence of synthetic diamond on said face is indicated.

23. A method of testing whether a natural diamond has had a layer of synthetic diamond deposited thereon, said diamond having a substantially symmetrical face, comprising:

directing a beam of ultraviolet radiation towards a face of the diamond at an angle substantially normal to said face, so as to form a pattern of beams of radiation due to refraction and reflection of the irradiating radiation; and observing the pattern of beams of radiation substantially of wavelength substantially in the range 230 nm to 320 nm, whereby if said observed pattern is grossly unsymmetrical, it is indicated that sides of said face are of different composition, one side being natural diamond, the other side being synthetic diamond.

24. A method of testing whether a natural diamond which has a table and a culet has had a layer of synthetic diamond deposited thereon, comprising:

directing a beam of ultraviolet radiation towards said table in a direction substantially normal to said table, so as to form a pattern of beams of radiation due to refraction and reflection of the irradiating ultraviolet radiation;

observing the pattern of beams of ultraviolet radiation substantially of wavelength substantially in the range 230 nm to 320 nm; and directing a beam of visible radiation towards said table in a direction substantially normal to said table, so as to form a pattern of beams of radiation due to refraction and reflection of the irradiating visible radiation;

observing the pattern of beams of visible radiation so produced;

directing a beam of ultraviolet radiation towards said culet, so as to form a pattern of beams of radiation due to refraction and reflection of the irradiating ultraviolet radiation;

observing the pattern of beams of ultraviolet radiation substantially of wavelength substantially in the range 230 nm to 320 nm; and distinguishing from said patterns of reflected and refracted radiation whether the diamond is a completely natural diamond, is a diamond with a layer of synthetic diamond deposited on the culet, or is a diamond with a layer of synthetic diamond deposited on the table.

25. A method of testing whether a natural diamond which has a table and a culet has had a layer of synthetic diamond deposited thereon, comprising:

directing a beam of ultraviolet radiation substantially of wavelength substantially in the range 230 nm to 320 nm towards said table in a direction substantially normal to said table, so as to form a pattern of beams of radiation due to refraction and reflection of the irradiating ultraviolet radiation;

observing the pattern of beams of ultraviolet radiation substantially of wavelength substantially in the range 230 nm to 320 nm;

directing a beam of visible radiation towards said table in a direction substantially normal to said table, so as to form a pattern of beams of radiation due to refraction and reflection of the irradiating visible radiation;

observing the pattern of beams of visible radiation so produced;

directing a beam of ultraviolet radiation substantially of wavelength substantially in the range 230 nm to 320 nm towards said culet, so as to form a pattern of beams of radiation due to refraction and reflection of the irradiating ultraviolet radiation;

observing the pattern of beams of ultraviolet radiation substantially of wavelength substantially in the range 230 nm to 320 nm; and distinguishing from said patterns of reflected and refracted radiation whether the diamond is a completely natural diamond, is a diamond with a layer of synthetic diamond deposited on the culet, or is a diamond with a layer of synthetic diamond deposited on the table.

* * * * *